United States Patent [19]

Jang

[11] Patent Number: 4,590,062

[45] Date of Patent: May 20, 1986

[54] DRY DIRECT COMPRESSION COMPOSITIONS FOR CONTROLLED RELEASE DOSAGE FORMS

[75] Inventor: Choong-Gook Jang, Short Hills, N.J.

[73] Assignee: Tech Trade Corp., New Brunswick, N.J.

[21] Appl. No.: 628,410

[22] Filed: Jul. 6, 1984

Related U.S. Application Data

[63] Continuation-in-part of Ser. No. 600,472, Apr. 16, 1984, abandoned, which is a continuation of Ser. No. 535,604, Sep. 26, 1983, abandoned, which is a continuation-in-part of Ser. No. 499,221, May 31, 1983, abandoned, which is a continuation-in-part of Ser. No. 419,409, Sep. 17, 1982, abandoned, which is a continuation-in-part of Ser. No. 316,993, Nov. 2, 1981, abandoned, which is a continuation-in-part of Ser. No. 147,929, May 8, 1980, abandoned, which is a continuation-in-part of Ser. No. 045,856, Jul. 5, 1979, abandoned, which is a continuation-in-part of Ser. No. 034,580, Apr. 30, 1979, abandoned.

[51] Int. Cl.$^4$ .......................... A61K 9/20; A61K 9/22; A61K 9/26

[52] U.S. Cl. .......................... 424/19; 424/22

[58] Field of Search .................... 424/14–22, 424/35, 38, 362, 365, 3

[56] References Cited

U.S. PATENT DOCUMENTS

| | | | |
|---|---|---|---|
| 3,062,720 | 11/1962 | Costello | 424/22 |
| 3,096,248 | 7/1963 | Rudzki | 424/32 |
| 3,115,441 | 12/1963 | Hermelin | 424/22 |
| 3,147,187 | 9/1964 | Playfair | 424/38 |
| 3,279,998 | 10/1966 | Raff et al. | 424/38 |
| 3,317,394 | 5/1967 | Fryklof et al. | 424/22 |
| 3,336,200 | 8/1967 | Krause et al. | 424/18 |
| 3,344,029 | 9/1967 | Berger | 424/19 |
| 3,362,880 | 1/1968 | Jeffries | 424/22 |
| 3,400,197 | 9/1968 | Lippmann | 424/21 |
| 3,402,240 | 9/1968 | Cain et al. | 424/22 |
| 3,432,592 | 3/1969 | Speiser | 424/19 |
| 3,577,514 | 5/1971 | Robinson | 424/22 |
| 3,950,508 | 4/1976 | Mony et al. | 424/19 |
| 3,965,256 | 6/1976 | Leslie | 424/22 |
| 4,167,558 | 9/1979 | Sheth et al. | 424/35 |

*Primary Examiner*—Shep K. Rose
*Attorney, Agent, or Firm*—Roland A. Dexter

[57] ABSTRACT

The selection of: a hydrophobic carbohydrate polymer, e.g. ethyl cellulose; and, generally at least one digestive-difficulty soluble component, i.e. a wax, e.g. carnauba wax, fatty acid material or neutral lipid provides upon dry direct compression a controlled and continuous release matrix for tablets or implants of biologically active agents. Preferred for producing dry direct compressed products is the combination of: a hydrophobic cellulose derivative; a wax, and, a fatty acid material and/or a neutral lipid since it provides upon dry direct compression a controlled and continuous release tablet or implant of improved structurally integrity against externally imposed forces.

8 Claims, No Drawings

DRY DIRECT COMPRESSION COMPOSITIONS FOR CONTROLLED RELEASE DOSAGE FORMS

REFERENCED APPLICATIONS

This is a continuation-in-part application of U.S. patent application Ser. No. 600,472 filed Apr. 16, 1984 which was a continuation of U.S. patent application Ser. No. 535,604 filed Sept. 26, 1983 which was a continuation-in-part of U.S. patent application Ser. No. 499,221 filed May 31, 1983 which was a continuation-in-part of U.S. patent application Ser. No. 419,409 filed Sept. 17, 1982 which was a continuation-in-part of U.S. patent application Ser. No. 316,993 filed Nov. 2, 1981 which was a continuation-in-part of U.S. patent application Ser. No. 147,929 filed May 8, 1980 which was a continuation-in-part of U.S. patent application Ser. No. 45,856 filed July 5, 1979 which was a continuation-in-part of U.S. patent application Ser. No. 34,580 filed Apr. 30, 1979, all of said applications having been abandoned.

BACKGROUND OF THE INVENTION

This invention relates to compositions and processes for making suitable controlled release dosage compressed forms of biologically active agents such as drugs, nutrients, pesticides, other biocides and fragrances. More particularly, it relates to a dry direct compression binder from hydrophobic carbohydrate polymers and to a mixture of a hydrophobic carbohydrate polymer and at least one water insoluble or sparingly soluble component composition as a dry, directly compressible matrix for controlled release of agents, particularly drugs and nutritional supplements, into the gastro-intestinal tract after oral ingestion of said composition or after implantation.

DESCRIPTION OF THE PRIOR ART

There is a recognized need for controlled release dosage forms of biologically active agents for humans and animals having the property of being released within the gastro-intestinal tract over a defined period of time and at a pre-determined rate of release after introduction of the agent into the body, as by oral ingestion of a tablet containing said agent or by implantation.

Various types of controlled release compositions have been developed and/or commercialized and can be classified according to at least the following three categories:

a. compositions in which granules or tablets containing a biologically active agent are coated with a water insoluble material, such as a wax or a synthetic resin (see U.S. Pat. No. 3,062,720);

b. compositions in which a biologically active agent is dispersed within a melt of water insoluble material (see U.S. Pat. No. 3,147,187) or is mixed with said water insoluble material and a water soluble material (see U.S. Pat. No. 3,577,514);

c. compositions in which a biologically active agent is held on an ion-exchange resin.

There are many disadvantages however in the preparation of such controlled release compositions.

The disadvantages are related to the fact that virtually all prior art compositions utilize a hydrophobic material to retard dissolution, disintegration or release of the biologically active agent. These hydrophobic materials are oftentimes hydrocarbons and their derivatives such as lipids, waxes, paraffins and hydrophobic polymers.

To retard the release of the biologically active agent by means of the hydrophobic material, virtually all these prior art compositions use heat or solvent to melt or dissolve the hydrophobic material and thereby achieve effective binding and desired release of the agent. Unfortunately the requisite use of heat or solvent results in related shortcomings, inconveniences and/or excessive costs of production. Attendant with the use of heat is: the risk that the biologically active agent may be harmed since many are unstable to heat; the fact that hot melting equipment is expensive and/or hazardous to operate; and, costly procedures of several additional processing steps.

Similarly, the use of a solvent is undesirable since the formulation can be easily tainted by a solvent residue which is not safe for human or animal ingestion, environmental pollution may attend the solvent removal step, occupational hazard may attend handling of the solvent and the biologically active agent may also be soluble in the solvent resulting in an undesirable dissolved system of release rather than the preferred dispersed controlled release system.

An approach to overcome the problems attendant with the heat or solvent processes would be to use a dry, direct compression process such as is taught in U.S. Pat. No. 3,279,998 wherein a blend of the biologically active agent and a micro-pulverized lipid, e.g. the fat, fatty acid, wax, etc., is compressed into tablets or in U.S. Pat. No. 3,577,514 wherein the biologically active agent is blended with a mixture of wax, enteric substance (acid-insoluble release agent) and water-soluble or dispersible binder. The requisite micropulverization of the lipid results in compression/adhesion difficulties for the former dry process whereas the latter process does not provide a system for controlled continuous release but rather a delayed release until an alkaline pH is reached.

Another approach to controlled release formulations have been to utilize physiologically tolerable synthetic resins having the property of flowing under high pressures to encapsulate the medicament (see U.S. Pat. No. 3,096,248) or to provide a skeletal matrix for tablet integrity during medicament release (see U.S. Pat. No. 3,317,394) or to provide a coating for active agents whereby said coated agents can be injection molded into medicaments in solid form (see U.S. Pat. No. 3,432,592). Unfortunately, this use of synthetic resins requires excessive (medicament injurious) temperatures and/or solvents so that these processes suffer the common disadvantages of the earlier discussed prior art approaches.

It is an object of this invention to provide a composition for the controlled release dosage forms of biologically active agents which overcomes the disadvantages of the prior art. More particularly, it is an object of this invention to provide a dry compression/adhesion-dry compressible binder and more preferably a combination of this dry binder and excipients that collectively cooperate to form a dry, compressible matrix which as the property of the controlled release dosage forms of biologically active solid particles dispersed throughout said matrix and a method of using said combination to obtain a controlled release tablet of useful integrity and desired release rates.

SUMMARY OF INVENTION

In my U.S. patent application Ser. No. 34,580, filed Apr. 30, 1979 it is taught that the combination of a hydrophobic cellulose derivative, a fatty acid material or a neutral lipid and a wax provides a matrix for particulate biologically active agent which can be dry compressed to provide a useful tablet having the property of controlled continuous release of said agent in the gastro-intestinal tract. It provides a composition adapted for controlling release of biologically active agents comprising and admixture of a fatty acid material or a neutral lipid, and preferably both, a wax and at least a binding amount of a hydrophobic cellulose derivative hereinafter defined as a hydrophobic carbohydrate polymer whereby said composition can be directly compressed in a dry state into tablet form having a hardness of 6 to 25 kg as measured on a Pfizer hardness tester.

More specifically, the aforesaid application teaches a controlled release formulation comprising from 0.01 to 95 wt. % of biologically active agent and from 5 to 99.9 wt. % of a controlled and continuous release binder admixture, said wt. % being based on the total weight of formulation and said admixture containing from 2 to 97 parts by weight of a fatty acid material or a neutral lipid and preferably both from 2 to 97 parts by weight of a wax preferably having a melting point between 60° C. and 90° C. and from 1 to 96 parts by weight of a hydrophobic cellulose derivative, i.e. a hydrophobic carbohydrate polymer. More particularly, the aforesaid application teaches that the described combinations: (a) a fatty acid material, particularly those of the class consisting of fatty acids having from 12 to 28 carbons, fatty monoalcohols having 12 to 28 carbons, fatty amines and amides having 12 to 28 carbons and mixtures thereof (e.g. an optimum mixture of 85 wt. % stearic acid and 15 wt. % palmitic acid) or a neutral lipid, particularly of the class consisting of stearin, palmitin, castorwax, phospholipids, glycolipids, glycerides such as glyceryl monostearate and glyceryl distearate, hydrogenated cottonseed oil, hydrogenated tallow and metal salts of $C_{12}$ to $C_{28}$ fatty acids, optimally hydrogenated cottonseed oil, or a mixture of said fatty acid material and said neutral lipid; (b) a wax preferably having a melting point between 60° C. and 90° C., particularly of the class consisting of carnauba wax, spermaceti, beeswax, candelilla wax, esparto and paraffins, optimally carnauba wax; and (c) a hydrophobic carbohydrate polymer, preferably of the class consisting of ethyl cellulose, propyl cellulose, cellulose acetate, cellulose acetate-butyrate, and cellulose acetate-propionate optimally ethyl cellulose; can be used to make controlled continuous release solid dosage forms of biologically active particulate agents by simple dry blending or slugging/granulation and compression (without a need of micropulverization, heat or solvent). The percentage of the active and the percentage of the combination in said formulation are readily varied to modify the controlled release rate of the active agent from a few hours to several days. The combination can be used for controlled release solid dosage forms of any particulate agent, preferably particles of less than 20 mesh in size.

In my U.S. patent application Ser. No. 54,856 filed July 6, 1979 the discovery was reported that the combination of the hydrophobic cellulose derivative (herein a hydrophobic carbohydrate polymer) in admixture with one of the digestive-difficulty soluble controlled release components, i.e. a fatty acid material, neutral lipid or wax, can be dry compressed with a particulate biologically active agent to provide a useful tablet having a hardness of 6 to 25 kg as measured on a Pfizer hardness tester.

It appears that the hydrophobic carbohydrate polymer synergistically cooperates with the digestive-difficulty soluble controlled release component, particularly with the fatty acid, to surprisingly strengthen the tableted combination containing the particulate biologically active material by imparting increased vertical strength and enhanced resistance to delamination from an external force.

The teachings herein now provide a controlled release dosage form that can be produced by a dry, direct compression process that overcomes the serious disadvantages of the prior art including the adverse and deleterious impact of solvents and/or heat which teachings result in compressed structures of surprisingly superior physical integrity and resistance to delamination.

DETAILED DESCRIPTION OF THE INVENTION

From the foregoing it must be evident that the invention herein relates to dry compressed products obtained from a directly compressible hydrophobic carbohydrate polymer and more preferably from a combination or an admixture of a hydrophobic carbohydrate polymer and various water insoluble ingredients which provide for controlled continuous release of the biologically active agent in the body when taken by mouth in tablet form or by implantation. The unique property provided by this admixture is one of dry compressibility so that useful tablets or implants can be readily produced in an inexpensive, facile, hazard free and environmentally safe manner.

BIOLOGICALLY ACTIVE AGENTS

The biologically active agents which can be admixed with the excipients to provide the controlled release tablets according to this invention include all substances which when introduced into the body of a human, animal, plants, soil and water is biologically active, usually in a therapeutic sense, nutritional purpose or biocidal effects.

Representative of such biologically active agents are:
a. vitamins, minerals and other nutritional supplements including all of the water soluble vitamins including Vitamin C, B vitamins and choline, inositol, bioflavinoids, iron, selenium, para amino benzoic acid, iodine, zinc, l-lysine, l-glutamine, l-cysteine, calcium, magnesium, potassium, etc.
b. ANALGESIC drugs such as acetaminophen, aspirin, codeine, salicylamide propoxyphene, pentazocine HCl, malbuphine HCl, ibuprofen, indomethacin, meperidine HCl, morphine and oxaprozin. ANOREXIC drugs such as amphetamines, phentermine, phenylpropanolamine and phenmetrazine. ANTHELMINTIC drugs such a peperazine citrate, pyrantel pamoate, thiabendazole, mebendazole, levamisole and their derivatives. ANTIASTHMA drugs such as terbutaline sulfate, isoetharine, theophylline and sodium glycinate. ANTIBACTERIAL drugs such as trimethoprim and sulfamethoxazole. ANTIBIOTIC and ANTIMICROBIAL drugs such as metropidazole, amoxicilli, erythromycin, ampicillin, penicillin, tetracycline, aminosalicylate, rifampin, cycloserine, amikacin, cefazolin, cephradine, ceflaclor, cephaloridine, chloroamphenicol, clindamycin, demeclocycline, kanamycin, cephaloridine, cefamandole nafate, cyclacillin, carbenicillin, vancomycin, cephradine, fluphenazine, hetacillin, streptomycin, ethambutol, methanamine, gentamicin and toburamicin. ANTICEPTIC drugs such as nitroflurantoin and sulfonamides. ANTICOAGULANT drugs such as warfarin. ANTICONVULSANT drugs such as clonazepam, nalproic acid, phenytoin, diazepam and primidone. ANTIDEPRESSANT drugs such as trimipramine maleate, imipramine HCl and impramine pamoate. ANTIDIABETIC drugs such as chloropropamide, acetohexamide, tolbytamide and tolazamide. ANTI-GOUT drugs such as probenecid, sulfinpyrazone and allopurinol. ANTIFUNGAL drugs such as griseofulvin, flucytosine, nystatin, clotrimazole and miconazole. ANTIHISTAMINE drugs such as triprolidine HCl, diphenhydramine HCl, chloropheniramine maleate, brompheniramine maleate and hydroxyzine HCl. ANTI-INFLAMMATORY drugs such as phenylbutazones, steroids, sulfonamides and salicylates. ANTIMALARIAL drugs such as chloroquine phosphate, hydroxychloroquine sulfate and pyrimethamine. ANTIMIGRAINE drugs such as ergotamine tartrate, propanolol HCl, isometheptene and mucate. ANTIMOTION SICKNESS drugs such as dimenhydrinate. ANTINAUSEANT drugs such as hydroxyzine HCl, buclizine HCl, prochlorperazine and promethazine HCl. ANTINEOPLASTIC drugs such as tamoxifen citrate, mitotane, megestrol acetate, tetolacone, flurouracil, busulfar, chlorambucil, melphalan, amsacrine, streptozocin, anthracyline agents, azacitidine, bleomycide, vinca allkaloids, cytrarabine, hexamethylmelamine, methotrexate, hydroxyaren, chlorotriansene, cisplatin, cyclophosphamide, decarbazine, dactinomycine, mithramycine, mitomycino, procarbazine, azathioprine, mercaptopurine, thioguanine and nitrosoureas. COUGH & COLD PREPARATION drugs such as quaifenesin, promethazine HCl, benzonatate, noscapine and dextromethorphan HBr. DECONGESTANT drugs such as brompheniramine maleate and henylephrine HCl. DIURETIC drugs such as thiazides, acetazolamide, furosemide and triamterene. HORMONE drugs such as estrogen, progesteron and the derivatives. MUSCLE RELAXANT drugs such as dantrolene sodium, cyclobenzaprine, clorozoxazone and quinine sulfate. PARASYMPATHOLYTIC drugs such as oxyphenomium bromide, atropine, hyoscyamine sulfate, glycopyrrolate and propanetheline bromide. SEDATIVE drugs such as barbiturates, meprobromate, promethazine HCl and methaqualone. TRANQUILIZER drugs such as diazepam, chloroazepate monopotassium, prazepam, chloridiazepoxide HCl and chloralhydrate.

c. AGRICHEMICALS including herbicides such as 2,4-D and its derivatives, class of nitrobenzen amines, prometrone, atrazine, simazine, trifluralin, picloram, lindane, batoxyethanolesters, dimethylamine, diquat silvex, tok, machete, lasso, avenge, prowl and their derivatives.
d. ALGICIDES such as chlorine compounds, e.g. calcium hypochlorite, and their derivatives.
e. ANTIFOULING AGENTS such as organotin compounds and organolead compounds.
f. FUNGICIDES such as kitazin and their derivatives.
g. INSECTICIDES such as DDUP, class of phosphoro thioate compounds, aldicarb, hexamethyl phosphoric triamide, malathion, parathion, pyrenium, sumithion, elsan, aldrin and their derivatives.
h. MOLLUSCICIDE such as copper bis(tri-n-butyltin)oxide, niclosamide and N-tritylmorpholine.
i. PHERMONES such as methyleugenol and grandlure.
j. PLANT GROWTH REGULATOR such as gibberelline and auxin.
k. RODENTICIDES such as decarboximide and their derivatives.
l. OTHER BIOCIDES
m. FERTILIZERS such as urea and other mineral nutrients
n. FLAVORS, FRAGRANCES, AND PERFUMES The kinds of biological agents for this invention are not limited to the names listed herein. Numerous other compounds can be incorporated into the excipients to make controlled release dosage forms according to the teachings herein.

The biologically active particulate solids which preferably should be smaller than 10 mesh (U.S. sieve grade), optimally pass through a 20 mesh screen, ranges broadly in an amount of 0.01 to 95, preferably 0.1 to 90, wt. % of the total formulation compressed into the controlled continuous release tablets. The dry directly compressible hydrophobic carbohydrate polymer binder or the admixture which makes possible the products of the invention provides a matrix for the biologically active particulate agent which ranges in an amount of 5 to 99.99, preferably from 10 to 99.9 wt. % based upon the total weight of said tablets derived from said compressed formulation. The dry directly compressible hydrophobic carbohydrate polymer of the admixture can also include as desired: flow aid materials in an amount ranging from 0.5 to 2 wt. %, said flow materials being represented by finely divided silica and talc; and from 0.5 to 2 wt. % of a lubricating material to facilitate tablet ejection e.g. a metal salt of a fatty acid, preferably magnesium stearate.

The combination of the invention which provides said matrix is either a dry directly compressible hydrophobic carbohydrate polymer or an admixture containing a hydrophobic carbohydrate polymer and a one to three digestive-difficulty soluble components readily produced by dry blending of powders smaller than 20 mesh, preferably 30 mesh, from the fatty acid material and/or the neutral lipid and/or said wax and the aforesaid hydrophobic carbohydrate polymer. The physiologically active particulate agent and additional excipients as desired are readily dispersed into the blended powders providing the matrix whereby the resultant formulation can be dry and direct compressed on a press under a pressure of 1.5 to 20, preferably 3 to 9, tons/square inch to produce the tablets. Under some circumstances it is useful to granulate the resulting tablets and recompress the granules with or without additional excipients to obtain the desired release rate. Tablets obtained from this teaching of the invention have a useful hardness, i.e. 3 to 25 kg as measurd on a Pfizer hardness tester, to provide a commercially marketable product.

HYDROPHOBIC CARBOHYDRATE POLYMER

The hydrophobic carbohydrate polymer constitutes from 1 to 100, preferably 3 to 50, optimally 5 to 30, wt. % of said matrix composition and provides said matrix composition with the integrity necessary to realize the binding of the controlled release tablets according to this invention.

Preferred hydrophobic carbohydrate polymers are those of the class of hydrophobic cellulose derivatives in which the R-moiety of the cellulose-R or cellulose-ROH or other R derivative is either an aliphatic acyl group of 2 to 22 carbons or aliphatic alkyl of from 1 to 8 carbons and chitin.

The most preferred hydrophobic carbohydrate polymers are ethyl cellulose, propyl cellulose, cellulose acetate, cellulose propionate, cellulose acetate-butyrate, cellulose acetate propionate. The optimum hydrophobic carbohydrate polymer is ethyl cellulose having an ethoxy content of from 43–50%.

DIGESTIVE-DIFFICULTY SOLUBLE COMPONENTS

As indicated above this invention has now taught that the hydrophobic carbohydrate polymer can be either singly used or in combination with a difficulty soluble component, i.e. any one or all of the components which are difficulty soluble in the digestive tract, i.e. wax, fatty acid and neutral lipid, which for purposes of this disclosure have been collectively designated the digestive-difficulty soluble component. Each has the property of slowly dissolving or disintegrating in the digestive tract.

1. WAX

The useful waxes are those which are obtained from plant and animal sources or as a petroleum product. In addition to its uses as a hydrophobic matrix material, the wax in this invention increases the hardness and compactness of the matrix, forming a cohesive hard tablet under the compressive forces of the process of this invention. The useful waxes have a melting point ranging from 50° C. to 100° C. and constitute from 0 to 99, preferably 5 to 70, optimally 10 to 40 wt. % of said matrix composition. Illustrative of the preferred waxes are carnauba wax, spermaceti, beeswax, paraffin wax as well as synthetic waxes e.g. polyethylene. The optimum wax is carnauba wax.

2. FATTY ACID MATERIALS

The fatty acid materials preferably along with the neutral lipid constitutes from 0 to 99, preferably 5 to 80, optimally 10 to 70, wt. % of the matrix composition of the invention which provides for controlled release of the active agent.

Fatty acid materials assist in the control or regulation of the rate at which release of the active agent occurs and are generally characterized by having a melting point above 43° C. The fatty acid materials preferably are of the class consisting of: fatty acids having 12 to 28 carbons, e.g. stearic acid, palmitic acid, lauric acid, eleostearic acid, etc.; fatty alcohols having from 16 to 44 carbons, e.g. stearyl alcohol, palmitol, etc.; a fatty amine having 13 to 45 carbons; and, a fatty amide having 11 to 45 carbons. A highly useful commercially available fatty acid material is Hystrene sold by Humko Sheffield (a division of Witco Chemical Co.) of Memphis, Tenn. which is a mixture of 85 wt. % stearic acid and 15 wt. % palmitic acid.

3. NEUTRAL LIPID

The neutral lipid which can be used as an alternative to a fatty acid material, but preferably in combination therewith constitutes from 0 to 99, preferably 5 to 80, optimally 10 to 70, wt. % of said matrix admixture of this invention. The neutral lipid cooperates with the fatty acid material in the control of the rate at which release of the agent occurs and is characterized by having a melting point greater than 43° C.

The neutral lipids are preferably of the class consisting of monoglyceride, diglyceride, triglyceride, phosphatides, glycolipids, steroids and neutral metal and organic salts of fatty acids having from 12 to 29 carbons. Representative examples of the preferred neutral lipids include stearin, palmitin, castor wax, lecithin, hydrogenated cottonseed oil, hydrogenated tallow, magnesium stearate and calcium and aluminum salts of palmitic and other fatty acids. A highly useful commercially available neutral lipid is hydrogenated cottonseed oil which has been obtained from: Humko Sheffield as Neustrene; Capital City Products as Ditrex or Sterotex; and Durkee as Lubritab.

As earlier noted it is taught herein that an optimum approach to admixtures which provide for dry and direct compression of controlled release dosage tablets and implants is for the admixture to comprise the combination of a hydrophobic carbohydrate polymer, a fatty acid material and/or a neutral lipid and a wax to serve as a matrix for the particulate biologically active agent.

Thus, the dry, direct compressed tablets and implants can be achieved by a composition adapted for controlling release of biologically active agents comprising an admixture of from 2 to 97 parts by weight of a fatty acid material of a neutral lipid and preferably both, from 2 to 97 parts by weight of a wax preferably having a melting point between 50° C. and 100° C. and from 1 to 96 parts by weight of a hydrophobic carbohydrate polymer.

The following examples demonstrate the practice and utility of this invention.

EXAMPLE 1

A controlled release tablet containing ascorbic acid as the biologically active agent was prepared as follows:

67.8 parts by weight of ascorbic acid having a particle size that passed through a 20 mesh screen was blended with 30.8 parts by weight of a mixture of 45.0 weight percent Hystrene, 24.4 weight percent Neustrene (a commercial product of hydrogenated cottonseed oil), 17.8 weight percent carnauba wax, 12.2 wt.% ethyl cellulose and 1.4 wt.% tableting excipients.

The resulting blend was passed through a 20 mesh screen and compression molded at a pressure of 3 to 9 tons per square inch into oval tablets containing 1000 mg of ascorbic acid and having a total weight of about 1530 mg, a thickness of about 7 mm and a hardness of about 14 Kg (measures on Pfizer hardness tester).

The controlled continuous release of tableted formulations obtained in this example is shown by the data of Table I. A number of tablets were subjected to a test in which a single tablet was placed in a beaker containing 100 ml of water maintained at 37° C. After a period of time, the tablet was taken from the water, the porous outer matrix of the test tablet was rubbed off until a solid core was left for drying and then air dried on a filter paper overnight. The solid core was then weighed. The consolidated results are hereinafter set forth in Table I.

TABLE I

| Time (hours) | % ascorbic acid released |
|---|---|
| 1.0 | 22 |
| 1.5 | 31 |

TABLE I-continued

| Time (hours) | % ascorbic acid released |
|---|---|
| 3.0 | 41 |
| 3.5 | 47 |
| 5.0 | 56 |
| 7.2 | 67 |
| 10.5 | 79 |
| 15.0 | 87 |
| 18.0 | 94 |
| 22.0 | 97 |

EXAMPLE 2

A controlled release tablet containing multi vitamins and minerals as biologically ctive agents was prepared as follows:

57.5 parts by weight of the blend of high potency multi vitamins and minerals having a size that passed through a 20 mesh screen was blended with 40 parts by weight of a dry direct compression mixture of 62.9 weight percent Hystrene, 17.4 weight percent Neustrene, 12.6 weight percent carnauba wax and 7.1 weight percent ethyl cellulose.

The resulting blend was passed through a 20 mesh screen and compression molded at a pressure of 3 to 9 tons per square inch into oval tablets having a weight of 1550 mg, a thickness about 6 mm and hardness of 15 kg (measured on Pfizer hardness tester).

90 weight percent of the tablet is disintegrated after 16.5 hours.

EXAMPLES 3-10

In each example, all the identified ingredients are sieved on a 20 mesh screen and blended together into a formulation. The formulation was then compressed on a tablet press to provide the controlled release tablets with the desired release times. The several examples with the respective formulations and corresponding time for disintegration of 90 weight percent of the tablet in 100 ml of $H_2O$ held at a constant 37° C. are set forth in Table II hereinafter set forth.

The data of the several examples show that the disintegration hence the release of these nutrients are continuous upon time. The release pattern is parabolic i.e. the rate, faster in the beginning and slower at the later times, which is often desirable for quickly achieving the desired blood level with subsequent prophylactic level for a prolonged period.

TABLE II

| | | Weight Percent of Total Formulation | | | | | | | | |
|---|---|---|---|---|---|---|---|---|---|---|
| Example Number | Biologically Active Agent | Active Agent | Ethyl Cellulose | Carnauba Wax | Hystrene[1] | Neustrene[2] | Inorganic Filler | Water Soluble Filler | Water Swellable Filler | $T_{90}$* (hrs) |
| 3 | Thiamine | 14.0 | 6.2 | 11.2 | 35.8 | 15.3 | 14.1 | — | 3.4 | 18 |
| 4 | Riboflavin | 14.4 | 5.4 | 9.8 | 34.8 | 13.3 | — | — | 22.3 | 10 |
| 5 | Calcium Ascorbate | 39.8 | 5.9 | 10.6 | 23.6 | 14.6 | — | — | — | 16 |
| 6 | Para Amino Benzoic Acid | 61.5 | 1.2 | 2.1 | 1.46 | 2.8 | 29.2 | — | 1.5 | 8 |
| 7 | Multi-Minerals | 73.5 | 4.0 | 7.2 | 5.0 | 9.8 | — | — | — | 10 |
| 8 | Iron as fumarate-gluconate-proteinate | 30.0 | 7.5 | 13.5 | 9.5 | 18.5 | — | — | — | 8 |
| 9 | Zinc as oxide-gluconate-proteinate | 24.0 | 8.1 | 14.6 | 10.3 | 20.1 | — | — | 21.7 | 8 |
| 10 | Pyridoxin HCl | 35.6 | 3.3 | 6.0 | 41.0 | 8.2 | 4.5 | — | — | 18 |

[1]Hystrene is a commercial mixture of 85 wt. % stearic acid and 15 wt. % palmitic acid
[2]Neustrene is hydrogenated cottonseed oil
*$T_{90}$ is the time required in hours for 90 weight percent disintegration of the tablet

EXAMPLES 11-13

Three controlled release tablet compositions containing ascorbic acid as the biologically active agent were prepared as follows:

Ascorbic acid having a particle size that passed through a 20 mesh screen was blended with three different formulas as set forth below.

Each of the resulting blends were passed through a 20 mesh screen and compression molded at a pressure of 3.1 tons per square inch into round convex tablets containing 35 mg of ascorbic acid and having a total weight of about 700 mg.

The blends in parts by weight are as follows:

| | Ex. 11 Blend | Ex. 12 Blend | Ex. 13 Blend |
|---|---|---|---|
| ascorbic acid | 49.26 | 49.26 | 49.26 |
| Hystrene[1] | 49.26 | — | 34.48 |
| Ethocel[2] | — | 49.26 | 14.78 |
| Magnesium stearate | 0.98 | 0.98 | 0.98 |
| Aerosil 200[3] | 0.49 | 0.49 | 0.49 |

1. Hystrene is a fatty acid mixture of 85 wt. % estearic acid and 15 wt. % palmitic acid sold by Humko Sheffield (a division of Witco Chemicals)
2. Ethocel is ethoxylated cellulose commercially available from Dow Chemical Company of Midland, Mich.
3. Aerosil 200 is a fumed silica sold by DeGussa, Inc. of Teterboro, N.J.

EXAMPLE 14

The tablets resulting from each blend of Examples 11, 12 and 13 had the following properties:

| Properties | Ex. 11 Blend | Ex. 12 Blend | Ex. 13 Blend |
|---|---|---|---|
| Color | Ivory White | Greenish White | White |
| Avg. wt. mg. | 720 ± 0.07 | 704 ± 0.05 | 704 ± 0.03 |

-continued

| Properties | Ex. 11 Blend | Ex. 12 Blend | Ex. 13 Blend |
|---|---|---|---|
| (10 tablets) Breaking pattern when subjected to opposed lateral horizontal force against tablet sides | delaminated horizontally in direction of force | crushed with vertical breaks | crushed with vertical breaks |
| Number of tablets horizontally broken (delaminated) out of a total of 20 tablets | 14 | 0 | 4 |
| Horizontal force required for breaking tablets - Pfizer Hardness kg (avg. of 20 tablets) | $8.2 \pm 0.7$ | $16.2 \pm 1.1$ | $10.4 \pm 0.9$ |
| Pfizer hardness kg when force is exerted vertically onto the convex face of the tablet (avg. 10 tablets) | $11.2 \pm 1.0$ | $13.9 \pm 1.1$ | $11.0 \pm 0.9$ |

The blends of Example 12 and 13, i.e. the blends of invention showed excellent hardness and was clearly superior in enhanced resistance to delamination forces.

The enhanced resistance to delamination makes possible ejection of the tablet from the tableting die cavity with reduced breaking of tablets arising from the delamination forces imposed on the tablet during ejection from the uneven walls of the cavity.

As will be seen from the Table III of Example 15, the composition of the invention provides useful controlled release of dosage forms of biologically active particulates.

EXAMPLE 15

The controlled continuous release of tableted formulations obtained from the blends of Examples 11–13 are shown by the data of Table III. Four tablets of each blend were subjected to a test in which a single tablet was placed in a breaker containing 100 ml of distilled water maintained at 37° C. After a period of time, the release medium was analyzed for the amount of ascorbic acid release from the tablets by the USP methods as published in the United States Pharmacopeia (20th Revision) Official from July 1, 1980 on page 55 of USP.

The percent of ascorbic acid released was calculated based upon the total quantity of ascorbic acid per tablet. Duplicate or triplicate release tests were performed and the average values were calculated. Also the porous outer matrix of the tablets was rubbed off until a solid core was left for drying and then air dried on a filter paper overnight. The solid core was then weighed. The consolidated results are hereinfter set forth in Table III as percent released.

The core method somewhat underestimating the amount ascorbic acid released is probably due to incomplete rubbing (figures in parenthesis).

Since the matrix controlled release can be expressed according to the authors of a well-known textbook (Controlled Release of Biologically active Agents, Edited by A. C. Tanquary & R. E. Lacey, Plenum Press, New York 1974) by the following equation:

$$\% \text{ released} = (t)^{\frac{1}{2}}$$

where k is a constant and t represents time in hours.

When the % released is plotted against the square root of the time, a straight line is obtained. Its slope is a good measure of release rates and experimental reproducibility of release rates. The time for 50% release ($t_{50\%}$) is also shown in the Table III by $t_{50\%} =$ $$\left(\frac{50\%}{k}\right)^2.$$

From Table III, fatty acids are the prolonged release rate controlling substance and the hydrophobic carbohydrate polymer, e.g. ethylcellulose, is poor for that purpose. However, ethylcellulose is an excellent dry direct compression tableting binder for controlled slow release tablets and as shown in hardness data and breaking pattern (Example 14), the presence of ethyl cellulose in dry-direct compression compositions does improve markedly the Tablet integrity by reducing delamination during the tablet compression, henceforth, the commercial controlled release tablet production.

The data of Example 15 shows that the slow dissolution, hence the release of biologically active particulates are, continuous upon time for a release admixture according to this invention while providing tablets of excellent strength and enhanced resistance to delamination.

Two blends comparable to the blends of Examples 11 and 13 were formulated except that carnauba wax was substituted for the Hystrene with the result that the modified blend of Example 13 according to this invention exhibited enhanced resistance to delamination from an external force. This was evidenced by tablets of the modified blend of Example 13 exhibiting an average breaking force of 11.3 kilograms (kg) whereas the tablets of the modified blend of Example 11 exhibited an average breaking force of 9.7 kg.

In the foregoing the components providing the matrix blend have been admixed in the dry blending stage. However, it is possible to provide one or more of the matrix blend components as a coating on the biologically active material and/or an excipient in the practice of this invention, e.g. introduce the ethyl cellulose as a coating on either or both into the dry mix blending step.

The hydrophobic carbohydrate polymer as described herein is exemplified in preferred form by cellulose polymers wherein the hydroxyl or charged groups of the molecule are modified, i.e. derivatized, into hydrophobic groups by alkylation, acylation or similar processes. Other suitable (for the purposes of this invention) carbohydrate polymeric substances which can be similarly derivatized to provide the essential hydrophobic property are starch, dextran, gums, inulin, mucopolysaccharides and chitin. In some applications the latter carbohydrate polymeric substances are themselves sufficiently hydrophobic to be used without further derivatization, e.g. chitin in its natural state possesses acetamido moieties which usefully modifies its cellulosic properties for use in matrix blends according to this invention.

During the investigation of excipients which can be introduced into the formulation of the invention, it has been discovered that then presence of 0.01 to 10, preferably 0.01 to 5, optimally 0.05 to 3, wt. % of hydrophobic fumed silica (a silica falling within the class of finely divided silica), said wt. % based on the total tablet weight, can surprisingly prolong the release rates by 20 to 40 percent as measured by t 100% (time to release 100% of the biologically active agents). Such prolongation can effectively reduced the amount of admixture necessary for dry direct compressible matrix to obtain desired release rates thus reducing the volume (size) of tablet required for a given dosage of biologically active material and/or increasing the amount of biologically active material per unit volume of the tablet.

|  | Ex. 16 Blend wt. % | Ex. 17 Blend wt. % | Ex. 18 Blend wt. % | Ex. 19 Blend wt. % |
| --- | --- | --- | --- | --- |
| Ascorbic Acid | 50.0 | 50.0 | 60.0 | 60.0 |
| Hystrene[1] | 32.0 | 32.0 | 25.3 | 25.3 |
| Ethocel[2] | 16.0 | 16.0 | 12.7 | 12.7 |
| CAB-O-Sil[4] N70TS | 1.0 | — | 1.0 | — |
| Aerosil 200[3] | — | 1.0 | — | 1.0 |
| Magnesium Stearate | 1.0 | 1.0 | 1.0 | 1.0 |

[1]As described for Exs. 11, 12, 13
[2]As described for Exs. 11, 12, 13
[3]As described for Exs. 11, 12, 13
[4]Cab-O-sil ® N70TS is a hydrophobic fumed silica sold by Cabot Corporation, Tuscola, Illinois.

TABLE III

| Time (hrs) | % ASCORBIC ACID RELEASED VS. TIME | | | | | | | | | |
| --- | --- | --- | --- | --- | --- | --- | --- | --- | --- | --- |
|  | EX. 11 BLEND | | | | EX. 12 BLEND | | | EX. 13 BLEND | | |
|  | Test #1 | Test #2 | Test #3 | Av. | Test #1 | Test #2 | Av. | Test #1 | Test #3 | Av. |
| 1 | 14 (15) | 14 | 14 | 14 ± 0.0 | 23 (23) | 26 | 24.5 ± 2.1 | 18 (14) | 18 | 18 ± 0.0 |
| 2 | 21.0 (19) | 19 | 24 | 21.3 ± 2.5 | 31 (28) | 35 | 33 ± 2.8 | 26 (19) | 26 | 28 ± 0.0 |
| 4 | 25 (27) | 26 | 28 | 26.3 ± 1.5 | 56 (45) | 50 | 53 ± 4.2 | 37 (30) | 34 | 35.5 ± 2.1 |
| 6 | 35 (33) | 33 | 35 | 34.3 ± 1.2 | 64 (61) | 61 | 62.5 ± 2.1 | 42 (37) | 43 | 42.5 ± 0.7 |
| k[1] |  |  |  | 14.1 ± 0.8 | 25.0 ± 1.3 |  |  |  |  | 17.9 ± 0.5 |
| t 50%[2] |  |  |  | 12.5 |  |  | 4.0 |  |  | 7.8 |

[1]wherein k is derived from slope of equation % released = k $(t)^{(j)}$

[2]$t_{50\%} = \left(\dfrac{50\%}{k}\right)$ = time in hours for 50% release.

HYDROPHOBIC FUMED SILICA

The hydrophobic fumed silicas are well known commercially available materials, e.g. Aerosil ® R-972 sold by Degussa, Inc. of Teterboro, N.J., Cabosil ® N70-TS sold by Cabot Corp. of Tuscola, Ill., Tullanox ® 500 sold by Tulco, Inc., (all of which are preferred for use herein), of the general class of amorphous precipitated silicas but of the pyrogenic (fumed) type which provides according to Kirk-Othmer's Encyclopedia of Chemical Technology (Third Edition) Vol. 20 at pages 768 and 778–779 an ultimate particle size, nm of 1–100 and an aggregate particle size, $\mu m$ of 2–3. The hydrophobicity of the fumed silica is achieved by replacement of the hydroxyl groups of the surface with $OR_5$ or $OOR_5$ wherein the $R_5$ moiety is 1 to 5 carbon aliphatic alkyl or aliphatic acyl groups. The most preferred hydrophobic silica is the methylated fumed silica. Hydrophobic silicas are discussed in Kirk-Othmer's Encyclopedia of Chemical Technology (Third Edition) Vol. 7 at pages 440–441.

Examples of blends containing hydrophobic fumed silica according to this invention are set forth in Examples 16 through 19 which follow.

EXAMPLE 20

The tablets of Exs. 16 through 19 blends were made according to the procedures of Examples 11 through 13 and thereafter measured for weight, thickness and hardness prior to evaluation of the release rates. The properties are shown in Table IV.

TABLE IV

| Physical Data of Tablets from blends of Exs. 16 through 19. | | | | |
| --- | --- | --- | --- | --- |
| Property (av. of 20 tabs.) | Ex. 16 Blend | Ex. 17 Blend | Ex. 18 Blend | Ex. 19 Blend |
| Weight (gr.) | 0.703 ± 0.008 | 0.702 ± 0.009 | 0.685 ± 0.009 | 0.704 ± 0.008 |
| Thickness (ins.) | 0.284 ± 0.002 | 0.281 ± 0.002 | 0.272 ± 0.001 | 0.274 ± 0.003 |
| Hardness (kg.) | 4.3 + 0.8 | 6.3 + 1.7 | 3.7 + 0.6 | 4.8 + 0.5 |

The release test data of the following Table V were obtained by analysis of the medium for ascorbic acid content. At each indicated time interval the release medium was replaced by fresh release medium and subjected to the analysis for Vitamin C content. Each of the release mediums were held at a constant 37° C. while exposed to the immersed tablet. Ascorbic acid release was analyzed by the USP XX methods. Release rates of tablets (av. of 4 to 6 tests) obtained from each of the blends of Exs. 16 through Ex. 19 are shown in Table V.

TABLE V

| | Total % Ascorbic Acid Released vs. Time | | | |
| --- | --- | --- | --- | --- |
| TIME (HRS) | Ex. 16 Blend | Ex. 17 Blend | Ex. 18 Blend | Ex. 19 Blend |
| 1 | 17.6 ± 0.9 | 20.4 ± 1.0 | 27.1 ± 0.4 | 29.2 ± 0.4 |
| 2 | 24.6 ± 1.1 | 28.6 ± 1.4 | 38.2 ± 0.7 | 44.7 ± 1.3 |
| 4 | 35.6 ± 1.2 | 39.8 ± 1.9 | 53.9 ± 2.1 | 65.9 ± 1.6 |
| 6 | 45.9 ± 2.6 | 49.3 ± 1.4 | 68.7 ± 3.5 | 75.0 ± 1.5 |

TABLE V-continued

| TIME (HRS) | Total % Ascorbic Acid Released vs. Time | | | |
|---|---|---|---|---|
| | Ex. 16 Blend | Ex. 17 Blend | Ex. 18 Blend | Ex. 19 Blend |
| 8 | 50.1 ± 2.0 | 55.8 ± 1.3 | 78.6 ± 2.9 | 84.8 ± 1.5 |
| k | 17.8 ± 0.5 | 20.1 ± 0.3 | 27.4 ± 0.5 | 30.9 ± 1.4 |
| $t_{100\%}$ | 31.6 ± 2.5 hrs | 24.8 ± 1.1 hrs | 13.3 ± 0.7 hrs | 10.5 ± 1.3 hrs |

$$t_{100\%} = \left(\frac{100\%}{k}\right)^2$$

The data of Table V shows that the presence of only 1% of the Cab-o-sil ® N70TS hydrophobic fumed silica increased the $t_{100\%}$ by 27% (the 6.8 hr. increase in the tablet of Ex. 17 compared with the tablet of the blend of Ex. 16 and similarly the 2.8 hr. increase in Ex. 19 over Ex. 18) for the tablets containing both 50 and 60 weight percent of ascorbic acid when it is added to the dry directly compressible mixture of this invention.

This dramatic increase in slowing release rates by a small amount is very important in perfecting controlled release tablets especially the tablet size.

In accordance with this invention, the presence of a small amount of hydrophobic fumed silica can be an effective dry controlled release agent when used in conjunction with other hydrophobic materials as taught herein.

The discovery of the remarkable utility of the presence of the hydrophobic fumed silica is applicable to other known controlled release processes such as those approaches earlier discussed in this application and the dry direct compression process using a micropulverized lipid, e.g. as described in U.S. Pat. No. 3,279,998 to produce tablets since its presence in said tablet in the amounts described herein will reduce the tendency of the tablet to desintegrate in water environments markedly reducing the dissolution rate. The 0.05 to 3 weight percent of hydrophobic fumed silica dispersed throughout the tablet as by blending the silica into the formulation prior to tableting provides lipid excipient controlled release tablets having better control of release, slower release if desired and improved physical integrity in aqueous environments such as found in the digestive tract.

EXAMPLE 21

The present dry direct compression process and compositions are applied to pharmaceuticals to make compressed controlled release dosage forms. The formula is shown in the following Table VI. These blends of dry blend compositions are directly compressed in standard rotary tablet press as before. The resultant directly compressed controlled release pharmaceutical tablets are subjected to release for the three hours in water having a pH of 3.0 and thereafter the pH was adjusted to 7.0 with the water temperature held constant at 37° C. The amounds of the drug released were measured by Perkin Elmer Lamda 3A doublebeam UV Spectrophotometer. The results are shown in the following Table VII. k and t100% (time for 100% release) were calculated according to the equation set forth in Ex. 15.

TABLE VI

| | Weight % of Various Pharmaceutical Controlled Release Tablets | | | | | | | | |
|---|---|---|---|---|---|---|---|---|---|
| | Active | Aerosil R-972 | Dritex | Hystrene | Carnauba Wax | Ethyl Cellulose | Aerosil 200 | Syloid 63 | Magnesium Stearate |
| Caffeine | 65.9 | | 12.4 | 6.3 | 9.1 | 5.0 | 0.2 | | 1.1 |
| Procainamide | 12.1 | 0.6 | 13.6 | 49.2 | 10.0 | 11.9 | 0.2 | 1.8 | 0.6 |
| Phenylpropanol Amine HCl | 15.2 | 0.8 | 14.2 | 45.2 | 10.4 | 13.3 | 0.2 | | 0.8 |
| Quinidine Sulfate | 42.0 | 1.4 | 7.9 | 32.0 | 5.8 | 10.2 | 0.1 | | 0.7 |
| Tetracycline | 35.1 | 1.1 | 10.5 | 33.5 | 7.7 | 11.3 | 0.2 | | 0.7 |
| Acetoaminophen | 61.6 | | | 9.5 | | 28.4 | | | 0.5 |
| Aspirin | 69.7 | | | | | 29.9 | | | 0.4 |
| Theophylline | 56.0 | 0.9 | 7.0 | 22.3 | 5.2 | 7.5 | 0.1 | | 0.9 |
| Sulfathiazole | 56.3 | 0.8 | 6.3 | 25.8 | 4.7 | 5.4 | 0.1 | | 0.6 |
| Dextromethorphan H Br | 14.1 | 0.6 | 15.9 | 43.4 | 11.7 | 13.4 | 0.3 | | 0.7 |
| Fluorouracil | 8.9 | 0.9 | 13.4 | 51.5 | 9.9 | 14.3 | 0.2 | | 0.9 |
| Nitroglycerine (1% lactose) | 49.0 | 0.5 | 7.3 | 23.4 | 5.4 | 12.8 | 0.1 | | 1.0 |

TABLE VII

| | % of Drug Released From Controlled Release Tablets of Table VI | | | | | | | |
|---|---|---|---|---|---|---|---|---|
| | Time (hr) | | | | | | | t 100% |
| Drugs | 1 | 2 | 3 | 4 | 5 | 6 | k | (hrs) |
| Caffeine (3) | 12.8 | 22.7 | 28.2 | 35.8 | 42.9 | 48.6 | 17.2 ± 2.7 | 34.0 |
| Procainamide (2) | 10.9 | 15.3 | 18.2 | 20.2 | | | 10.7 ± 0.4 | 87.3 |
| Phenylpropanol Amine HCl (3) | 17.1 | 29.1 | 40.0 | 49.6 | | | 21.6 ± 3.4 | 21.4 |
| Quinide Sulfate (3) | 5.7 | 9.5 | 12.5 | 15.2 | 17.3 | 19.4 | 7.3 ± 0.9 | 187 |
| Tetracycline (2) | 5.7 | 7.1 | 7.9 | 8.5 | 8.9 | 9.2 | 4.6 ± 0.7 | 472 |

TABLE VII-continued

| Drugs | % of Drug Released From Controlled Release Tablets of Table VI | | | | | | k | t 100% (hrs) |
|---|---|---|---|---|---|---|---|---|
| | Time (hr) | | | | | | | |
| | 1 | 2 | 3 | 4 | 5 | 6 | | |
| Acetoaminophen (2) | 5.9 | 11.1 | 16.1 | 22.1 | 25.3 | | 8.9 | 126 |
| Aspirin (2) | 2.1 | 4.2 | 6.2 | 8.4 | | | 3.3 ± 0.9 | 920 |
| Theophylline (2) | 3.6 | 6.6 | 8.7 | 11.0 | | | 4.7 ± 0.8 | 452 |
| Sulfathiazole (2) | 0.9 | 1.5 | 2.1 | 2.5 | 2.3 | 3.2 | 1.2 ± 0.2 | 6944 |
| Dextromethorphan HBr (3) | 5.4 | 9.2 | 12.3 | 15.1 | 17.8 | 20.1 | 7.1 ± 1.0 | 198 |
| Fluorouracil (3) | 0.7 | 1.1 | 1.4 | 1.6 | 1.9 | 2.1 | 0.8 ± 0.1 | 15625 (651 days) |
| Nitroglycerine (1% lactose) (2) | 4.1 | 7.7 | 10.6 | 13.7 | 16.4 | 18.9 | 6.3 | 252 |

Number in ( ) next to drugs indicates number of release tests on each type.

EXAMPLE 22

As an example for an algicide controlled release tablet form, calcium hypochlorite tablets were prepared according to the present invention as follows.

| | wt. % |
|---|---|
| Calcium Hypochlorite | 74.3 |
| Dritex | 9.3 |
| Hystrene | 4.7 |
| Carnauba Wax | 6.8 |
| Ethylcellulose | 3.7 |
| Aerosil 200 | 0.1 |
| Magnesium Stearate | 1.0 |
| | 100% |

Release rates were measured by immersing the tablet into room temperature water for 10 minutes and dried for 20 minutes and repeated this process 10 times as if the tablet was soaked with water only during the swimming pool filtering periods. The result shows an average 1% of the active component release each time. This rate will permit 100 times soaking of the tablet for each 10 minute period or 100 days for 10 minutes soaking each day.

PRODUCTS OF THE INVENTION

Tablets formed by the new dry direct compression process are very different from the tablets formed by known processes using solvents, heat or plastic polymers. The tablets of the invention can be distinguished from the products of known processes by the following criteria:
1. Detectability of chemical compounds not supposed to be present in the finished product, such as heat degraded compounds or solvent residues;
2. Physical structure differences;
3. Release rate profile differences;
4. Identification of components.

The known processes set forth in U.S. Pat. Nos. 3,317,394, 3,432,592, 3,344,029, 4,167,558, 3,402,240, 3,062,720, 3,577,514, 3,147,187, 3,965,256 and 3,362,880 result in products which are fully distinguishable by the above criteria from the tablets of the invention.

Many commercial defects and shortcomings as controlled release tablets are very apparent in the tablets resultant from the very complicated prior art processes. The tablets of the inventive dry direct compression process overcome those defects and shortcomings with a simple, easy and extremely low cost process. The aforesaid defects and shortcomings are amplified hereafter.

1. Detectability of Hazardous Chemical Compounds

Previous processes using heat to make controlled release tablets deactivate the biologically active components resulting in reduced potency of the active and cause chemical reactions, oftentimes of a totally unknown nature. Many biologically active compounds are highly sensitive to the exposure of the heat required to melt or glassify hydrophobic lipids and polymeric material used as controlled release medium (see U.S. Pat. Nos. 3,147,187, 3,432,592, 3,317,394, 3,344,029 and 3,965,256).

Not only is the instability of the biologically active compounds a shortcoming but also the degraded or deactivated or chemically newly formed compounds is potentially hazardous to human and animal health, to plant life and the environment. The present dry direct compression process hardly has any chance to form such potentially hazardous compounds and does not produce tablets of reduced potency.

The amounts of impurities in the tablets of the present process is only limited to the amounts of impurities present in raw material according to the supplier's specifications often by the certificates of analysis after dilution factors. For example, if ascorbic acid has 0.01% impurity and if the ascorbic acid content is 50% of the tablet weight then total percent of impurity for the tablet becomes 0.005%. The amounts of impurities in raw material drugs and food additives are limited by USP or Food Chemicals Codex specifications. Ranges of purity by assay are 99.0%–100.0% (some examples: acetaminophen, 100.4%, procainamide HCl, 99.3%, ascorbic acid, 99.5%, lobeline sulfate, 100.3%, 1-glutamine, 99.9%, pyridoxine HCl, 99.8%, etc.).

The reduced potency and the presence of the newly formed compounds are easily detected by common analytical procedures using UV, IR, GLC, GC, HPLC, NMR and other residue analysis methods.

Heat degradation of the biologically active components can occur during the solvent removal step for the processes using solvents (see U.S. Pat. Nos. 3,362,880, 3,147,187, 4,167,558 and 3,344,029).

Especially the degradation of the biologically active components is more pronounced in the presence of water at elevated temperatures (see U.S. Pat. Nos. 3,362,880, 3,965,256, 3,062,720, 3,402,240). The presence of moisture in the tablet from processes using water accelerates the degradation of many active components in finished product.

Thus a comparison of stability data will also distinguish the product of present process.

Another undesirable chemical component present in the tablets of the prior processes are solvent residues. The product of the present dry direct process is free of solvent residues.

Again the amounts of solvent residues are only limited to those of raw material before compression after volume/weight dilution factors. Most raw material certificates of analysis state loss after drying as the amount of volatile compounds (organic solvents or water) (see Table VIII for representative compounds).

Products from the known processes using solvents have solvent residues no matter how effective the solvent removal process. The solvent residues can be easily detected by standard analytical techniques.

When the solvent contents and types are analyzed for the finished tablets, the dry directly compressed tablets show only amounts of those inherited from raw material as shown in Table VIII.

TABLE VIII

Typical Solvent/Moisture or volatile matter contents of active and matrix components according to manufacturer's specifications used for this invention.

|  | Loss on Drying | Moisture |
|---|---|---|
| Hystrene | No solvent residue | <0.01% |
| Carnauba Wax | No solvent residue | <0.5% |
| Dritex | <0.1% |  |
| Ethylcellulose | <0.5% | <2.0% |
| Aerosil R-972 |  | <0.5% |
| Aerosil 200 |  | <1.5% |
| Cabosil N70-TS | <1.0% |  |
| Pyridoxine HCl | Negligible |  |
| Choline Bitartrate | <0.21% |  |
| Niacinamide | Negligible |  |
| Inositol | <0.03% |  |
| Acetaminophen | <0.07% |  |
| Procainamide HCl | <0.3% |  |
| Phenylpropanolamine HCl | <0.5% |  |
| Lobeline Sulfate | <0.1% |  |

On the other hand, tablets of prior arts using solvents show higher amounts of those solvent residues in addition to the types and amounts inherited from raw material. Those prior teachings using solvents include U.S. Pat. Nos. 3,344,029, 3,062,720, 3,147,187, 3,965,256 and 3,362,880. These are potential hazards to health and environment of the residual solvent. Many solvents used in the prior art such as dichlorethylene (U.S. Pat. No. 3,147,187), benzene (U.S. Pat. No. 3,317,394), carbon tetrachloride (U.S. Pat. No. 3,344,029), and methylene chloride are known to cause cancer in animals and humans. U.S. Pat. No. 3,344,029 uses methyl alcohol which is highly toxic.

2. Physical Structure Difference

Because the heat or solvent process involve physicochemically liquid states, products resulting from the prior process using such have physical structures of tablets very different from the product made by the present dry direct process which only involves solid states. These physical structure differences can be examined mainly under three different aspects.

Heat fusion and solvent solution of lipid or hydrophobic polymeric material both result in a more homogeneous liquid state. Cooling or solvent removal forms mass interlinked agglomerated skeletal structure with crystal or solid state structures changed from the original dry particle structures before the treatment.

First, interlinked skeletal structures are evident after the active components are leached out. The empty honeycomb of fused or glued binders and lipid or polymer material have much stronger structures than those of the present dry direct process with identical wt. % compositions. The product of the present process easily crumbles to the particle size of the precompression state. This is particularly the case for hydrophobic carbohydrate polymers. Change in crystal structures or morphology after heat/solvent process are easily detected by x-ray diffraction and electron microscopy. Especially the extent of crystallinity in polymers are reduced due to the presence of solvent residues with their plasticizing effect (see U.S. Pat. Nos. 3,362,880 and 3,344,029).

The easier crumbling and disintegration of the excipients are more desirable for the environment. Tablets which are unbreakable or difficult to crumble and retain the structure after leaching as by passage through the gut will give doubt to consumers of the incomplete release of the biologically active agents when viewed in the stool by the user. Such are the products of U.S. Pat. Nos. 3,432,592, 3,317,394, 3,147,187, 3,344,029 and 3,062,720. This physical structure difference is also easily examined by a polarizing microscopic technique. The thin cross sections of the tablets provided by the dry direct process of the invention shows clear cut boundaries between particles and crystals of composition components with the size and shapes the same or closely similar (allowing compression shrinkage of hydrophobic carbohydrate polymers) to the sizes and shapes of the precompression state. Those products using heat/solvent give fused together or glued together structures markedly different from the pretreatment state.

More amorphous and less crystalline states are also detected by a polarizing microscope with far less clear boundary between excipients. The particle size after treatment usually depends on sieve sizes of the granulation processes used for prior art processes. A less clear boundary between the active and controlled release materials and change of particle size, crystal forms of the biologically active component are also observed due to melting and solubilization of the active by heat or solvent common to solubilize both the active and controlled release material. Ethanol and water are typically such solvents which are used to dissolve both active and controlled release materials. For example aspirin has solubility of 1 g/100 cc in $H_2O$ and 1 g/5 cc in ethanol. The prior art process using ethanol to dissolve ethylcellulose will dissolve also aspirin and after drying alter the crystal structures. Shape and size of the aspirin become different from those of pretreatment state. X-ray diffraction, electron and polarizing microscopes detect the changes resulting from the solvent process (see U.S. Pat. Nos. 4,167,558, 3,402,240, 3,965,256, 3,062,7820, 3,317,394, 3,432,592, 3,362,880, 3,344,029 and 3,147,187).

Co-melting by heat and co-solubilization by solvents of the active and the controlled release material also changes crystal structure of the controlled release material by formation of a solid solution or a eutectic mixture. X-ray diffraction, electron microscope, polarizing microscope and thermal analysis techniques easily detect such changes. On the contrary the present dry direct process preserves the physical characteristics of the active and controlled release material intact and native to precompression state when observed by these techniques.

Electron and polarizing microscopic examinations of the tablet from the present dry direct process show even distribution of the active and lipid and hydrophobic carbohydrate polymer components in the matrix structure. Tablets of the prior art process using heat and solvent show that greater concentration of the controlled release material around the active component to be coated. An examination of the products of: U.S. Pat. Nos. 3,965,256 and 3,317,394 will show that the lipid material coats the active component; and, U.S. Pat. Nos. 4,167,558, 3,062,720, 3,362,880, 3,344,029 and 3,147,187 show that hydrophobic polymer coated the active agent forming completed or partially encapsulated forms. Such coating by lipid or hydrophobic polymers is not present in the tablet of the present process. Where the prior art process has two steps of first encapsulating the active and then dry mixing with other filler or lipid material, then by using differential solvents which dissolve only the second step material, one can isolate the active-encapsulating material combination and examine it by microscope or IR and thermal analysis technique. The tablets of the present process do not have such partially or completed encapsulated structure and with the above differential dissolving method the active agents and the hydrophobic material become physically separated.

3. Release Rate Profile Difference

The tablets of the present dry direct process are a true matrix system where the active component particles are evenly and truly dispersed between dry direct composition components without solubilizing into each other. On the other hand, tablets of the prior art processes due to heat fusion/solvent solubilization between the active and the controlled release material contain solid solutions and eutectic mixtures as explained before.

The release profiles of the biologically active components in biological fluid medium, i.e. water or gastric juice, are different since the products of the invention provide a dispersed system whereas the products of the prior art products provide a partially or completely dissolved system as illustrated by R. W. Baker and H. K. Lonsdale in p. 40.1 Controlled Release Symposium 1974 published by the University of Akron, Akron, Ohio.

For a dispersed system the release profile can be presented as $$M_t = A(2D\ C_sC_o)^{\frac{1}{2}} t^{\frac{1}{2}} = k_1 t^{\frac{1}{2}} \quad (1)$$

$$t_{100\%} = \frac{l^2 C_o}{8DC_s} = k_2;\ \text{a finite number} \quad (2)$$

For a dissolved system the release profile can be presented as $$M_t = M_{100\%}\left(1 - \frac{8}{\pi^2} e^{\frac{(-\pi^2 Dt)}{l^2}}\right) \quad (3)$$

$$= M_{100\%}(1 - k_3 e^{-k_4 t})$$

$$t_{100\%} \to \text{Infinite} \quad (4)$$

Where $k_1$, $k_2$, $k_3$ and $k_4$ are constants and
Mt = amount release at time t
A = Surface area
$C_s$ = Solubility in the dispersed medium
$C_o$ = The initial concentration in the device
l = thickness of the device
D = diffusion constant
$t_{100\%}$ = Time for 100% release or exhaustion time
$M_{100\%}$ = 100% content of the active By examining the release profiles, tablets using above mentioned prior art processes give extremely long $t_{100\%}$ at a very low ineffective level as $M_t$ follows an exponential rate (see equations 3 & 4) (dragging on) whereas the tablets of the present process give clear cut end points (see equations 1 & 2). Illustrative diagrams of these two systems for release profile are included in the above Baker and Lonsdale's publication. Those products of the prior art which form solid solutions are described in U.S. Pat. Nos. 3,317,394, 3,432,592, 3,344,029, 4,167,558, 3,402,240, 3,062,720, 3,147,187, 3,965,256 and 3,362,880.

4. Identification of Controlled Release Components

Tablets of prior art processes are also distinguished from the tablet of present process and compositions by identification of controlled release material. U.S. Pat. Nos. 3,317,394 and 3,432,592 use a single thermoplastic or injection moldable polymeric material. Many prior art processes such as in U.S. Pat. Nos. 3,147,187, 3,976,256 and 3,302,880 use water swellable hydroxycellulose or hydrocolloid polymers as binders. U.S. Pat. No. 4,167,558 uses a hydrocolloid as buoyant material. All these water swellable polymers can be identified by a standard analytical method. U.S. Pat. No. 3,402,240 uses glucose, a simple sugar as a binder. The present process does not use such polymers or glucose as binder or buoyant material. U.S. Pat. No. 3,279,998 uses dry direct compression process with only micropulverized lipid material without any hydrophobic carbohydrate polymer.

The directly compressed tablets of U.S. Pat. No. 3,577,514 using an enteric substance are easily distinguished from the tablets of the present process. The former does not release the biologically active component in the acid pH and release only in the medium of alkaline pH. The present process tablet releases the active continuously regardless of pH conditions. The former therefore can not be used as controlled release dosage forms. The present new process of direct compression with dry blend controlled release compositions without heat and solvent procedures produces very different controlled release tablets from those obtained from published processes. The product of the present process should be able to be easily distinguished in the market places from those of the prior art processes. Analytical tools and methods for differentiation are UV, IR, Fourier Transform IR, NMR, Solid State NMR Spectroscopics, X-ray diffraction, light, electron and polarized microscopy, mass spectroscopy, thermal analysis, gas chromatography, high pressure liquid chromatography, other residue analysis methods and release test methods.

What is claimed is:

1. A dry, direct compressed product containing controlled release dosage forms of therapeutically active particulate agents and produced without heat or solvents by the steps comprising: (a) dry blending blend particles of a particle size smaller than 20 mesh and consisting essentially of from 0.01 to 95 parts by weight of biologically active particulate solids with from 5 to 99.99 weight parts of a matrix blend combination consisting essentially of from 1 to 96 parts by weight of a hydrophobic carbohydrate polymer selected from the group consisting of ethyl cellulose, propyl cellulose, cellulose acetate, cellulose propionate, cellulose acetate-butryate and cellulose acetate-propionate and from 4 to 99 parts by weight of a digestive-difficulty soluble component selected from the group consisting a wax selected from the group consisting of carnauba wax, spermceti, beeswax, candelilla wax, esparto and paraffins; a fatty acid material selected from the group consisting of fatty acids having from 12 to 28 carbon atoms, fatty monoalcohols having 12 to 28 carbon atoms, and fatty amides and amines having from 12 to 28 carbon atoms; a neutral lipid selected from the group consisting of stearin, palmitin, castorwax, phospholipids, glycolipids, glycerides, hydrogenated cottonseed oil, hydrogenated tallow and metal and organic salts of fatty acids having from 11 to 28 carbon atoms; and, mixtures thereof into a first blend; (b) compressing said first blend under a pressure of 1.5 to 20 tons per square inch; and, (c) thereafter, recovering said first blend as a compressed product having a hardness of 4 to 25 kg and excellent resistance to delamination when subjected to an external longitudinal force.

2. A product according to claim 1 wherein: said hydrophobic cellulose polymer is ethyl cellulose present in from 3 to 50 parts by weight; said wax is carnuba wax present in from 5 to 70 parts by weight; said fatty acid material is a mixture of stearic acid and palmitic acid; said neutral lipid is hydrogenated cottonseed oil; and, said fatty acid material or said neutral lipid or both is present in from 5 to 80 parts by weight.

3. A dry, direct compressed product according to claim 1 wherein said hydrophobic polymer is ethyl cellulose present in from 5 to 30 weight parts and the balance of said combination being selected from the group consisting of carnauba wax, hydrogenated cottonseed oil, a fatty acid having from 12 to 28 carbons or mixtures thereof.

4. A product according to claim 1 wherein said recovering is followed by the further steps of (d) granulating said compressed product to granules, (e) blending said granules with additional excipient particles into a second blend, (f) compressing said second blend into bodies with desired release rates and (g) recovering said bodies as said compressed product.

5. A product according to claim 1 wherein said mixtures of said digestive-difficulty soluble component comprises from 2 to 97 parts by weight of said wax and from 2 to 97 parts by weight of said fatty acid material, of said neutral lipid and of mixtures thereof.

6. A product according to claim 1 wherein: said polymer is present in from 5 to 30 parts by weight; said wax is present in from 10 to 40 parts by weight; said fatty acid material is present in from 10 to 70 parts by weight; and, said neutral lipid is present in from 10 to 70 parts by weight.

7. A product according to claim 1 wherein said blended particles of step (a) additionally contain from 0.01 to 10 weight parts of hydrophobic fumed silica whereby the dissolution release rate is reduced.

8. A product according to claim 7 wherein said silica amounts to from 0.05 to 3 weight parts.

* * * * *